United States Patent [19]

Arnegger

[11] Patent Number: 4,513,742

[45] Date of Patent: Apr. 30, 1985

[54] SAW BLADE WITH APERTURE

[76] Inventor: Richard E. Arnegger, Rietlirain, 8713 Uerikon, Switzerland

[21] Appl. No.: 418,070

[22] Filed: Sep. 14, 1982

[30] Foreign Application Priority Data

Oct. 13, 1981 [CH] Switzerland .................. 6523/81

[51] Int. Cl.³ .............................................. A61B 17/14
[52] U.S. Cl. ...................................... 128/317; 30/350; 30/351; 83/835
[58] Field of Search ................... 128/317; 83/835; 30/351, 350

[56] References Cited

U.S. PATENT DOCUMENTS

| | | | |
|---|---|---|---|
| 692,184 | 1/1902 | Kline | 128/317 |
| 1,689,618 | 10/1928 | Brown | 83/835 |
| 3,852,881 | 12/1974 | Treace | 128/317 |
| 3,905,105 | 9/1975 | Tuke | 128/317 |
| 3,905,374 | 9/1975 | Winter | 83/835 |
| 3,952,412 | 4/1976 | Rhodes | 128/317 |
| 4,257,301 | 3/1981 | Tuomaala | 83/835 |
| 4,324,163 | 4/1982 | LaVelle | 83/835 |

FOREIGN PATENT DOCUMENTS

| | | | |
|---|---|---|---|
| 1066954 | 11/1952 | France | 83/835 |
| 2460127 | 2/1981 | France | 128/317 |
| 29565 | of 1913 | United Kingdom | 83/835 |

*Primary Examiner*—C. Fred Rosenbaum
*Assistant Examiner*—Gene B. Kartchner
*Attorney, Agent, or Firm*—Donald D. Denton

[57] ABSTRACT

The present invention covers a saw blade having a row of teeth with a unique arrangement along its edge and the blade has at least one closed aperture which extends in the direction away from the row of teeth, wherein the part of the saw blade between the row of teeth and the aperture comprises a strip-like element.

10 Claims, 9 Drawing Figures

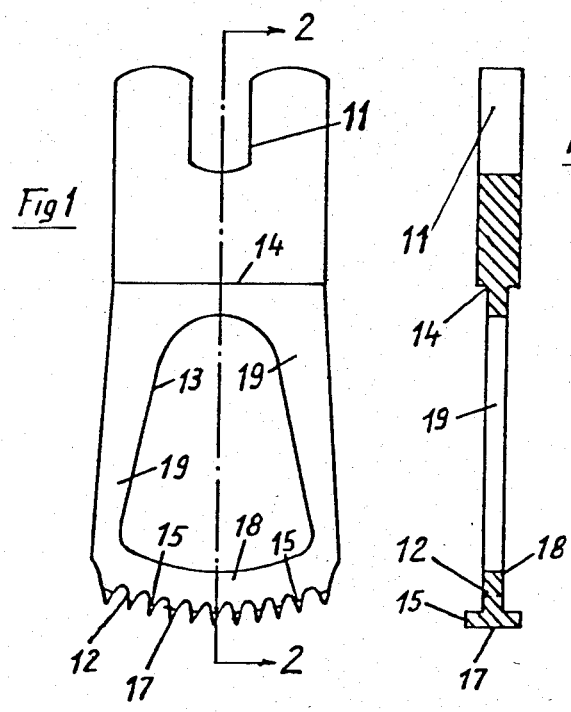
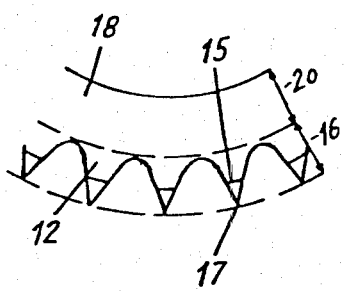
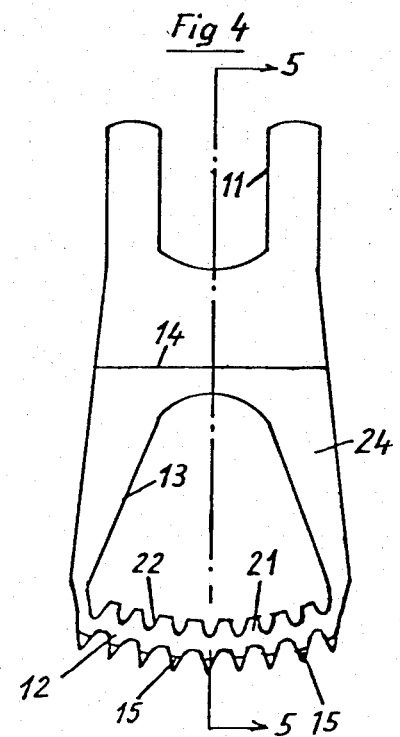
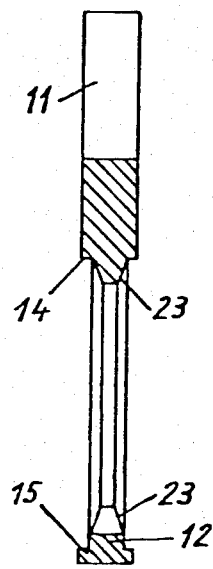

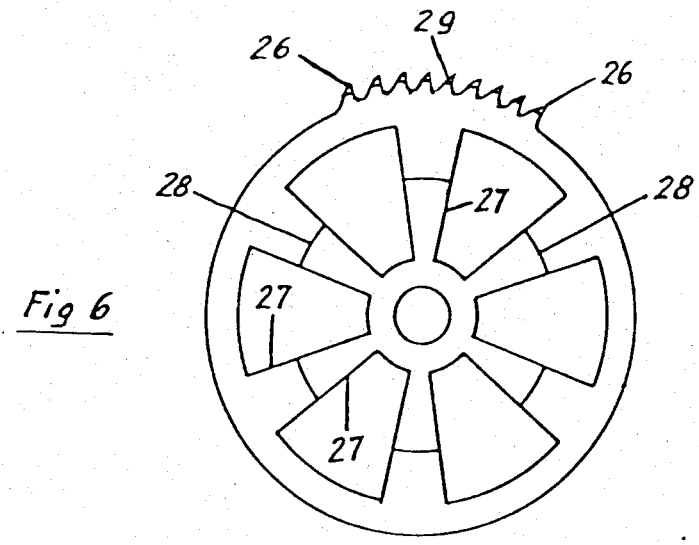
Fig 6
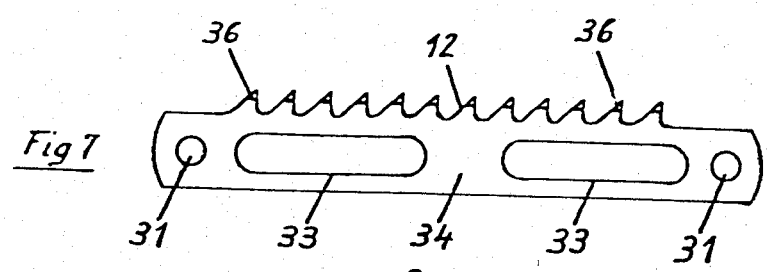
Fig 7
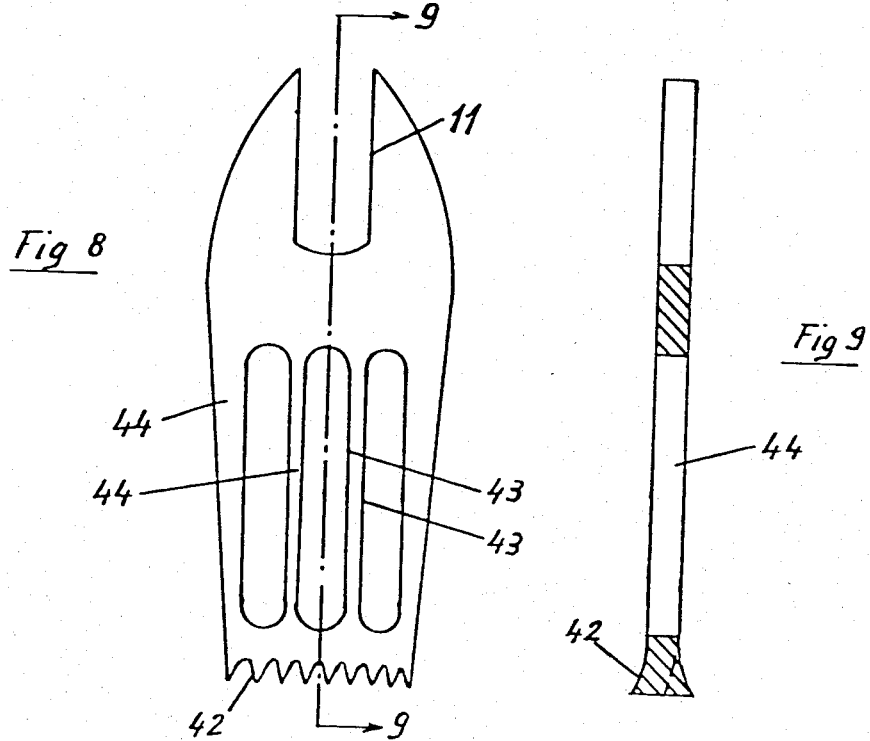
Fig 8
Fig 9

SAW BLADE WITH APERTURE

BACKGROUND OF THE INVENTION

The present invention relates to a saw blade with a row of teeth with a unique arrangement along its edge. It is characterized in that the blade has at least one closed aperture which extends in the direction away from the row of teeth, wherein the part of the saw blade between the row of teeth and the aperture comprises a strip-like element.

It is known in the art that in a sawing process saw chips or saw dust, i.e. saw waste, is produced with the waste hindering the cutting process. The saw chips can stick to the saw blade and produce a strong friction between the saw blade and the material to be cut. This leads to clamping and to a detrimental warming up. It is also known that the saw dust will weld onto the side sectios and round sections. This is the so-called cold-welding.

SUMMARY OF THE INVENTION

These disadvantages are to be avoided according to this invention, which is characterized in that the saw blade has at least one closed aperture, which extends in the direction away from the row of teeth, wherein the part of the saw blade between the row of teeth and the aperture comprises a strip-like element.

In particular, in the field of bone surgery a cool cutting, as obtained by the inventive device, is of great importance. As a consequence of the provision of an aperture, the surface of the saw blade exposed to friction with the object to be sawn is markedly reduced. Thereby, in the cutting process of a bone, there will result less bleeding of the adjacent tissue, so that the view of the cut is much better. Thereby, cuts of the highest precision are possible and in addition the subsequent healing process is speedier. It is also important that, as a consequence of the presence of the aperture, there is always enough room for saw chips or saw dust, thus avoiding a compound of bone dust. If it is necessary to use a rinsing with a fluid, the sterile fluid can flush the bone dust away. It is not necessary that the fluid run down the sidewalls of the blade; it will enter directly into the aperture. A corresponding process applies to a cooling fluid in an industrial use.

BRIEF DESCRIPTION OF THE DRAWINGS

These and other objects of the invention will become apparent from the following description of preferred embodiments and the drawings, in which:

FIG. 1 is a front view in elevation of a saw blade for an oscillating saw;

FIG. 2 is a side view in cross-section along the line 2—2 of FIG. 1;

FIG. 3 is a partial view of enlarged teeth of the saw blade according to FIG. 1;

FIG. 4 is a front view of another embodiment of an oscillating saw blade of this invention;

FIG. 5 is a cross-section along the line 5—5 of FIG. 4;

FIG. 6 is a front view in elevation of a circular saw blade of this invention;

FIG. 7 is a front view of a saw blade having the teeth of this invention in the form of a hack saw;

FIG. 8 is a front view in elevation of another example of an oscillating saw blade; and FIG. 9 is a cross-section along the line 9—9 of FIG. 8.

DESCRIPTION OF THE PREFERRED EMBODIMENTS

The saw blade shown in the FIGS. 1, 2, and 3 has an indentation of indent 11 which serves to fix the blade to the saw and to drive it by a motor. The saw blade has along its edge a row of teeth 12. The blade has a closed aperture 13; this means the aperture 13 is all around surrounded by the blade body. On each side of the blade face there is a shallow section, which extends from the border line 14 to the border line 15 at the teeth 12, which is located over a part of height 16 (FIG. 3) of the teeth 12. The points 17 of the teeth 12 are therefore thicker than is the thickness of the teeth 12 in between the line 15 and the base of the teeth. They are aso thicker than is the thickness of the saw blade between the teeth 12, respectively, the border line 15, and the border line 14.

Thus it can be seen that the provision of an aperture 13 appreciably reeuces the surface of the blade which comes into contact with the material to be cut, as compared with a full blade or blade body. If, after the sawing process, the row of teeth 12 and its strip-like element 18 have passed through the cut, a friction can take place only at two arms 19. Therefrom there result the above-mentioned advantages of a cool cut and an improved surgical working condition. Under normal conditions it is of advantage if, as shown in FIG. 3, the height 16 of the teeth 12 is approximately equal to the width of the element 18.

In view of the specific construction of the teeth, they do not have to be set. They are arranged parallel to the center plane, which is parallel to the side faces of the blade. Therefrom there results that the blade, in comparison to regular blades with a setting, has practically no vibration during operation. This again means that this sort of saw blade is particularly well suited to be provided with an aperture.

The embodiment shown in FIGS. 4 and 5 has again an indent 11 for the fixation and the drive of the saw blade. The latter is again provided with a row of teeth 12 along its outer edge. As shown in the foregoing example, an aperture 13 is provided. Between the border lines 14 and 15 and on both side faces of the saw blades there is a shallow section which extends at the location of the teeth 12 outwardly over a part of their height.

A strip-like element 21 carries a row of teeth 12 and indentations 22, each of which is in registry with a tooth. It is seen that in this way the surface contacting during cutting will be even smaller and the weight of the blade will be even lighter than it is in the embodiment shown in FIGS. 1, 2, and 3.

According to the embodiment of FIGS. 4 and 5, the edge of the aperture 13 is bevelled, which means the edge has a broken rim 23 as can be seen in FIG. 5. This bevelled rim can extend over the entire perimeter of the aperture 13 or only over a part of it. This bevelling causes the edge to be more resistant and stronger. The formation of hair cracks in the blade material is thereby reduced. The formation of hair cracks in the blade material can also be reduced if the indentations 22 are rounded, in particular at their deepest location. The same is true for the base of the teeth 12. The widening of the indentations 22 in the direction away from their deepest location and toward the aperture 13 causes the saw chips to be moved in the direction toward the aperture 13. They will, therefore, move only slightly into the area between the element 21 and the teeth 12 and the cutting faces of the object to be sawn.

The aperture 13 shown in FIG. 4 has a form tapered in the direction away from the element 21, which is shaped similar to an isosceles triangle, of which the base line extends along the row of teeth 12. The structure shown in FIG. 4 represents a stable saw blade, which is free from vibrations and has comparatively small sidefaces. According to the circumstances and particularly for deep cuts, in lieu of the blade shape of FIG. 4, an aperture 13 of a form may be chosen in which the entire length of the arms is substantially equal to the width, which the arms of FIG. 4 have in the neighborhood of element 21, i.e. the arms over their entire length are of constant width.

Another embodiment is shown in FIG. 5 in the form of a circular saw blade which is provided with teeth 25 over its entire perimeter. Additionally there is provided a plurality of apertures 27. Also, this blade has on its upper and lower side face a shallow section. The shallow section shown in FIG. 6 extends from the borderline 28 toward the outside in such a way that it will include the part of the height of the teeth up to the border line 29. While it is known that with a circular saw a great deal of the saw chips is moved away sideways, the apertures 27 still add to the fact that a smaller amount of saw dust will get between the sides of the blade and the sides of the cut. Particularly, in a mutual contact of the side faces and the cut, for instance due to an inaccurate guiding of the saw, less heat is produced, because with a circular saw blade, relatively little surface is present which will cause friction. The circular saw serves in particular for industrial use.

The saw blade according to FIG. 7, which is still a further embodiment, is for a hack saw. The blade is tightened with the holes 31 to a bow (not shown). Along a longitudinal edge of the saw blade there is provided a row of teeth 12. A bridge 34 is provided between two apertures 33. On each side face of the saw blade there is a shallow section. These shallow sections extend from the border lines 36 over the entire width of the blade, i.e. to the longitudinal side of the blade opposite to the teeth 12. This kind of blade also is intended mostly for industrial use.

Still another embodiment is shown in FIGS. 8 and 9 and relates again to an oscillating saw. It has again an indent 11. Three apertures 43 extend in the direction away from the eeth 42. The apertures are limited on the sides by arms 44, which are to improve the stability, in particular to reduce vibrations, and to keep the row of teeth 42 in a straight line. As can be seen in FIG. 9, this blade has no shallow sections, but its teeth 42 are set. Also with a saw blade with set teeth, the provision of an aperture has the advantage of reduced obstructions by the saw chips, of less friction and therewith a cool cutting. The cold welding of chips is practically avoided.

The present invention is also applicable to saw blades with a wavy setting.

In using a saw blade of hardened steel, it is very important that in the manufacture of the blade the hardening process is made first and the aperture in the blade is made afterward. A warping of the blade is thereby avoided. The waste pieces resulting from the production of the apertures can be used as valuable basic material for other kinds of tools.

Also, in the use of a blade according to the invention there result the advantages that the waste chips stick less onto the blade so that the detrimental heating up of the blade, the jamming and the decrease of the quality of the cut are prevented or greatly reduced. In particular, in bone surgery the resulting cool sawing process is of high value. Additionally, the tissue coming into contact with the saw blade is less subject to bleeding.

Applicant is the owner of application for U.S. Letters Patent Ser. No. 394,187 filed July 1, 1982, entitled "Saw Blade With Shallow Section," the disclosure of which is made a part of this application by way of reference.

Although the invention is described in detail for the purpose of illustration, it is to be understood that such detail is solely for that purpose and that variations can be made therein by those skilled in the art without departing from the spirit and scope of the invention except as it may be limited by the claims.

What is claimed is:

1. A thin plane saw blade for an oscillatory saw having at least a partial rotational action when in use for use in bone surgery, said saw blade having a distal end portion comprising: side faces parallel to a center plane of said blade; an outer edge located at the distal end portion of said blade; a row of teeth extending along a portion of said outer edge, the distance between said outer edge and the distal edge of the teeth defining a tooth height; at least one closed aperture which extends in the direction away from the row of teeth, the portion of the blade between the aperture and the row of teeth comprising a strip-like element, the distance between said aperture and said outer edge being uniform along the entire length of the strip and defining a strip height, said strip height being at most twice the tooth height; said saw blade aperture being of a form which is symmetrical with respect to a median plane arranged perpendicularly to said center plane, passing through the middle of the row of teeth and bisecting said aperture, the saw blade and its teeth being made of a single piece of hardened steel plate of which the closed aperture arrangement was worked out of the already hardened steel plate.

2. The saw blade according to claim 1 in which the teeth are unset and have a cutting portion and a base portion and on each of the said faces of said blade there is provided a recessed portion which extends to the row of teeth and over said base portion and part of the height of the teeth, the surfaces of the recessed portions being parallel to each other.

3. The saw blade according to claim 1 in which the aperture extends along the whole row of teeth.

4. The saw blade according to claim 1 in which a plurality of apertures are extending away from the row of teeth.

5. The saw blade according to claim 3 in which, in the case of an oscillating saw blade having a row of teeth arranged along a portion of its outer edge, the aperture is tapered in the direction away from the row of teeth.

6. The saw blade according to claim 4 in which the saw blade is in the form of a hack saw blade having along a portion of a longitudinal edge a row of teeth, the blade provided with apertures separated by a bridge and extending away from the row of teeth close to the opposite longitudinal edge of the hack saw blade.

7. The saw blade according to claim 4 in which the saw blade is circular in form and has a row of teeth arranged along its entire perimeter with a plurality of apertures provided, each of which extends away from a portion of the row of teeth and is tapered in the direction toward the center of the saw blade.

8. The saw blade according to claim 1 in which the aperture is limited at least partially by a broken edge.

9. The saw blade according to claim 5 in which the aperture approximately has the shape of an isosceles triangle, the base line of which is arranged along the row of teeth.

10. The saw blade according to claim 1 in which the strip-like element arranged between the row of teeth and the aperture, on the side of the aperture, is provided with trough shaped indentations which are in registry with the teeth and rounded at their deepest location and are widening in the direction away from their deepest location toward the aperture.

* * * * *